United States Patent [19]

Hill

[11] Patent Number: 4,457,750

[45] Date of Patent: Jul. 3, 1984

[54] MICROPROCESSOR CONTROLLED INTRAVENOUS FEED SYSTEM

[75] Inventor: Charles C. Hill, Del Mar, Calif.

[73] Assignee: Luther Medical Products, Inc., Costa Mesa, Calif.

[21] Appl. No.: 317,440

[22] Filed: Nov. 2, 1981

[51] Int. Cl.³ .............................................. A61M 5/16
[52] U.S. Cl. ........................................ 604/65; 222/58; 364/415; 128/DIG. 13
[58] Field of Search ........... 128/213 R, 214 R, 214 E, 128/214 F, 214.2, 260; 137/486, 487.5; 222/58; 364/413, 415; 604/65–67

[56] References Cited

U.S. PATENT DOCUMENTS

| | | | |
|---|---|---|---|
| 3,977,567 | 8/1976 | Rudd | 222/39 |
| 4,111,198 | 9/1978 | Marx et al. | 364/413 |
| 4,211,340 | 7/1980 | Szakasits et al. | 222/3 |

Primary Examiner—Edward M. Coven
Attorney, Agent, or Firm—Willie Krawitz

[57] ABSTRACT

A control system for an intravenous feed tube is provided that functions by sensing weight changes with respect to time, i.e., dw/dt, of an intravenous solution supplied to a patient, the solution being maintained as a free hanging load. The weight changes are detected by strain gauge sensors, and then applied as signals to a microprocessor that is programmed to produce suitable control responses. These responses are fed to a motor which applies a constrictive force to the intravenous tube and maintains the solution flow at the desired rate.

20 Claims, 6 Drawing Figures

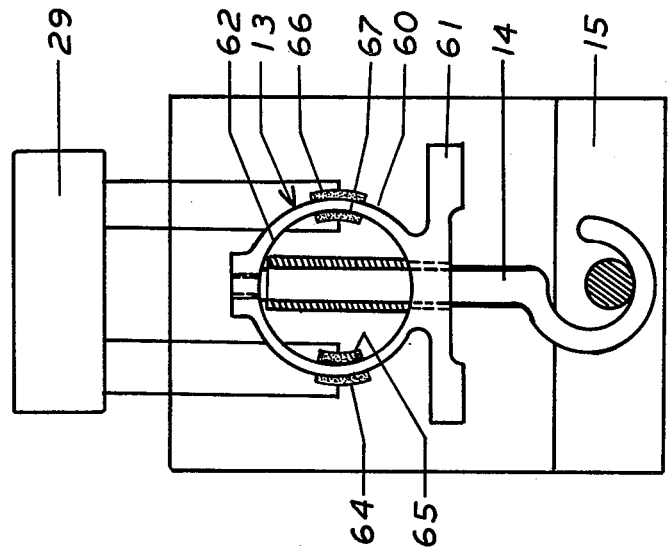
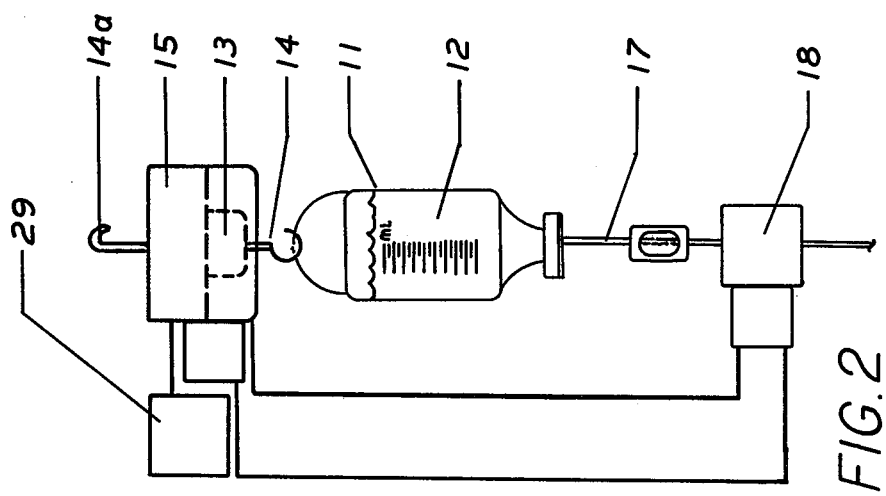

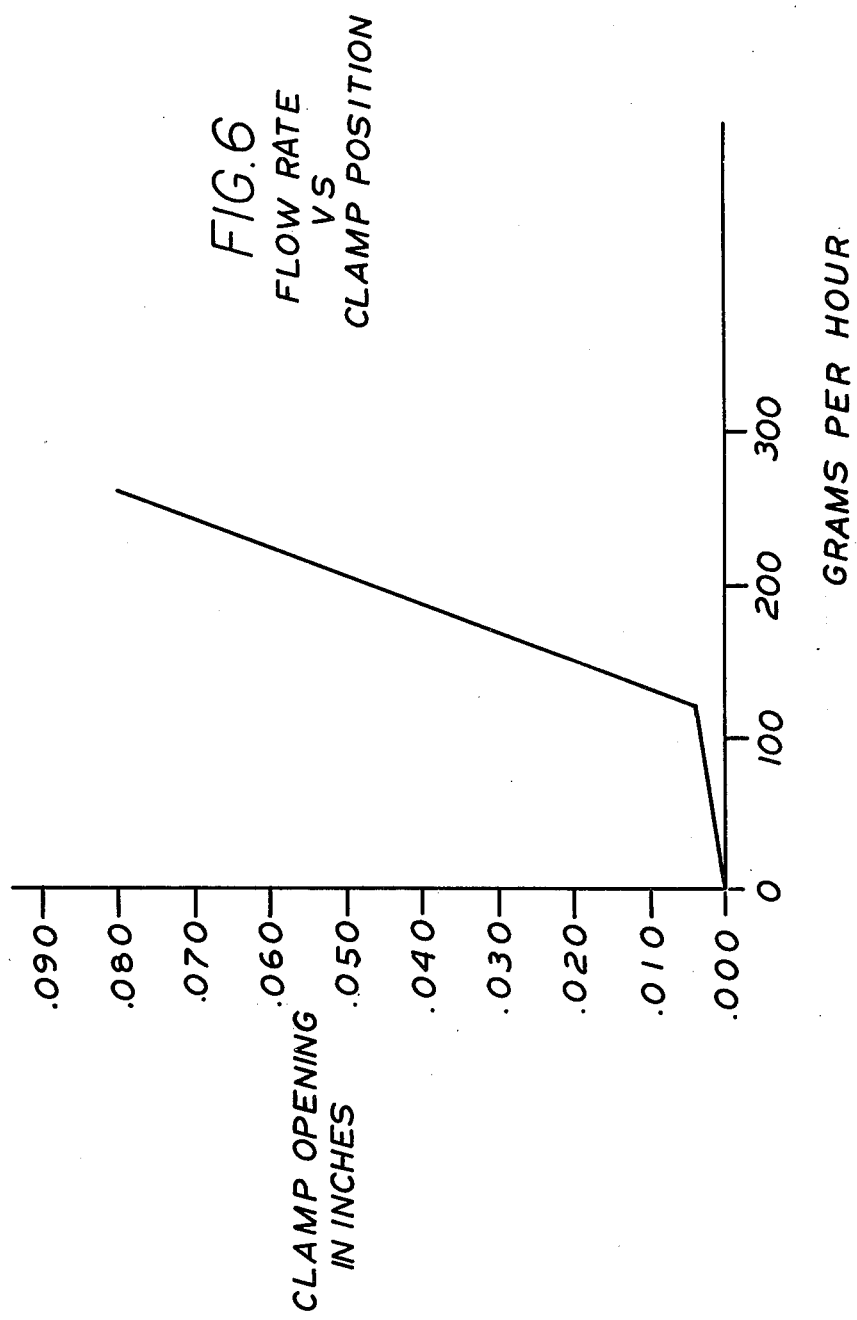

MICROPROCESSOR CONTROLLED INTRAVENOUS FEED SYSTEM

BACKGROUND OF THE INVENTION

This invention relates to a new and improved control system for adjusting the amount of intravenous solution supplied to a patient based on the rate of weight change of a free hanging load of the solution. A close control of solution feeding rate can be thereby achieved.

As intravenous therapy becomes an increasingly important aspect of patient care, it is important that for many procedures, flow rates must be precisely and safely maintained. Intravenous solutions and additive programs have become more complex, with greater variances in the types of solutions and drugs being administered through intravenous equipment. Fluid balance maintenance is required for many pos-operative patients, pediatric patients, obstetric patients, mental patients, cancer patients, burned patients, and patients with traumatic injuries. In addition, total parenteral nutrition is rapidly gaining momentum, and the administration of nutrients is a prime indication for the use of controlled infusions as are the administration of antibiotics, anticoagulants, electrolytes, labor inducing drugs, and others.

Various feed control systems for intravenous devices are known, and most include a drop counting method. However, these devices are sensitive to variations in drop size caused by temperature and viscosity, drop rate and manufacturing inaccuracy of the drop platform. Another type of I.V. flow control device utilizes a positive displacement, speed controlled pump, but this requires an accurate tolerance of pump components, which is expensive. Usually, commercial intravenous control devices presently claim an accuracy of about 2%-5% for pumps, and a 1%-2% drop rate accuracy for controllers, and both types are fairly expensive.

There is desired a relatively low cost intravenous control device providing constant and precise flow rates. The device should be immune to changes in temperature and viscosity and flow rate as they affect drop size, and should not require disposable components made to a close tolerance. The device should prevent dry and runaway I.V.s.

THE INVENTION

According to the invention, there is provided a control system for an intravenous feeding tube that functions by measurement, such as by one or more strain gauges, of weight changes with respect to time, i.e., dw/dt, of a free hanging load of the intravenous fluid. The dw/dt measurements are compared in a microprocessor with a preset, adjustable, flow rate, and usually the total amount of fluid to be administered. Signal information from the microprocessor is applied to a constriction device that controls the flow through the intravenous feeding tube. Use of gravity feed in conjunction with the strain gauge measurement, the microprocessor signal processing, and the closely controlled constriction device for the feed tube obtains the desired flow control. Undesirable problems usually associated with gravity feed and a simple clamp control are reduced significantly; these problems frequently involve inaccurate flow rates, and dry and runaway I.V.s. Optionally, the controls can be set to slow down the amount of fluid delivered to the patient at or near the end of the infusion to prevent a dry I.V.

Control of material delivery systems by means of weight changes in the feed supply to control an effluent valve are well known in the chemical process industry, but this technology has not been adapted to control an intravenous feed tube to a patient in accordance to the invention. One advantage of the present control system is that the major components are relatively inexpensive, and some are commercially available. Also the components employed in this invention do not require close tolerance machining. Furthermore, the control system of this invention may be employed with existing I.V. administration sets.

BRIEF DESCRIPTION OF THE DRAWINGS

FIG. 2 is an external view in side elevation showing the free hanging container with intravenous fluid, weight sensor, and constriction means for the intravenous tube;

FIG. 5 is a sectional view in side elevation showing the details of the weight sensing means; and, FIG. 6 is a graph showing the relationship between flow rates and constriction openings, typical for an I.V. tube set.

DESCRIPTION OF THE PREFERRED EMBODIMENTS

Figure 1:
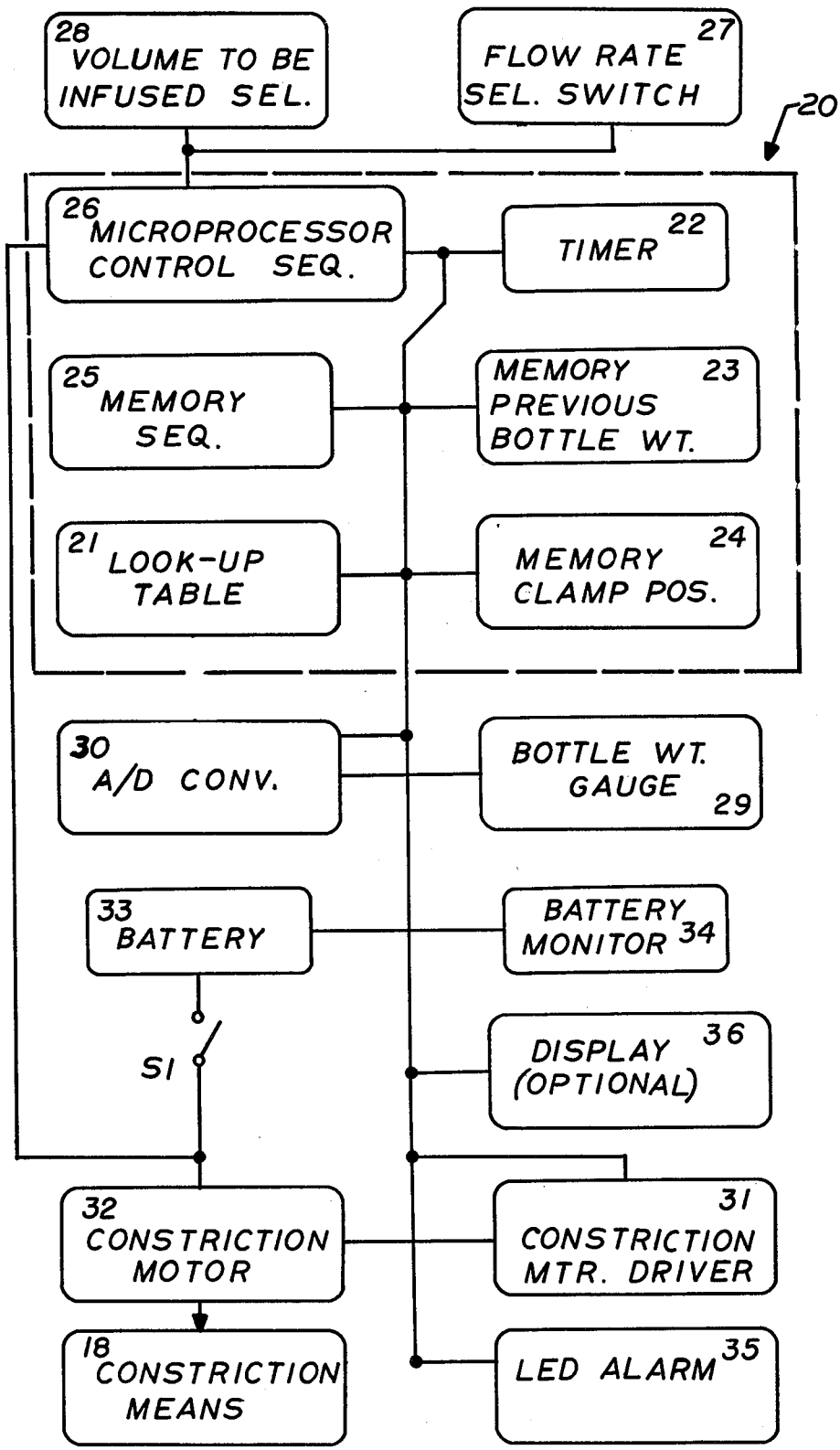
FIG. 1 is a block of the electrical components and also the constriction means of this invention.

The control and intravenous delivery system of this invention is shown in FIGS. 1 and 2, and includes an intravenous fluid container 11 holding an intravenous fluid 12. The container 11 is freely supported from a load cell 13 by a support hook 14. The load cell itself is enclosed in a housing that is supported by a hook 14a, and the housing includes a control panel 15. An intravenous tube 17 is gravity fed from the container 11 and passes through a constriction means 18 that regulates movement of fluid through the tube. The constriction means is one of the features of this invention, and will be more fully described, infra. The intravenous tube 17 is attached at its free end to a catheter which is inserted into a patient's vein.

The block diagram of the system used to process signal information from the load cell 13 to drive the constriction means 18 is shown in FIG. 1. The system comprises a microprocessor 20 shown in dotted designation, such as a Motorola MC 146805 G2/E2. One microprocessor is described in the publication: "Motorola Semiconductors, Advance Information MC146805E2", published August, 1981, and, "Take 5ive MC146805E2 8-Bit Microcomputer Programming Guide", published September, 1981, both by Motorola Semiconductor Products Inc. The microprocessor includes a look-up table 21 for determining the positioning of the constriction means 18 with respect to the tube 17, and is based on the same or similar data as shown in the graph of FIG. 6.

A timer 22 is used, among other things, to measure increments of time ($\Delta t$), used to obtain an average weight at the beginning and end of each time increment. The time increments are usually measured over intervals of about ½ minute to several minutes.

An initial weight measurement is made at the end of a time interval, and a second weight measurement is made about 0.1 second later. If the two measurements are equal, a valid weight is assumed. However, if the measurements are not equal, indicating possible interfering vibrations from a mechanical disturbance, additional measurements are made until two successive measurements are equal. Subtraction of weights obtained at the end of each $\Delta t$ interval will thereby produce a good $\Delta w$ reading. The net result is that short term perturbations of the equipment will not disturb the readings. Consequently, over reasonably short $\Delta t$ increments, $\Delta w/\Delta t \rightarrow dw/dt$, and this will determine the revised constriction settings based on the look-up table 21.

Memories 23, 24 are accumulating registers that store the latest container weight and constriction positions respectively. A sequencing memory 25 is a ROM, which in conjunction with the CPU, generates ordered address words relating to various operations, e.g., display, constriction motor drive, low battery reading, arithmetic unit, alarm function, etc. A control sequencer 26 generates program step pulses or jump pulses depending on the particular program address word in the sequence memory 25, and routes these pulses to access and control the specific operation. Thus, data from the look-up table 21, the control sequencer 26, and the various readings are fed to the sequence memory 25 and converted into ordered address words; these are then fed to the control sequencer 26 and routed to the various operations.

An arithmetic unit functions to determine $\Delta w$, $dw/dt$, compare the measured $dw/dt$ with the preset $dw/dt$, and determine the revised constriction settings based on the look-up table 21.

Flow rate settings are dialled from a flow rate selector switch 27, and the amount of solution to be fed is dialled from a control switch 28; both sets of information are fed to the control sequencer 26. Container weight 29 obtained from a strain gauge reading is converted 30 from analogue to digital using an integrated circuit such as an Intersil ICL 7135 and fed to the look-up table 21. The constriction position is based on its previous position and the flow rate error and will be varied depending on the strain gauge reading, the rate of weight change of the container obtained from memory 23, and on constriction information from memory 24. Pulses for a current constriction position are fed to the constriction motor driver 31 and then to a constriction motor 32 in the constriction means 18. The entire system may be operated by a battery 33 as indicated, due to the low power requirements of the system, the battery being connected to the system through a switch, S1. A battery monitor 34 is used to indicate a low battery condition.

A set of LED indicator lights 35 in the control panel 15 provides warning in case of a low battery, complete infusion, and excessive or inadequate flow rate. An excessive flow rate usually indicates a leak, while inadequate flow rate usually indicates a blockage. An optional display 36 in the control panel 15 may be used to indicate the volume of intravenous fluid 12 that has been delivered. Alternatively, the volume delivered may be simply read from volume markings on the fluid container 11. When the preset weight approaches or equals the final weight, the flow may be maintained open, but at a low rate, e.g. 10–30 ml/hr., to keep the patient's vein open, thereby conserving the remaining fluid in the container and preventing a dry I.V. line.

Figure 4:
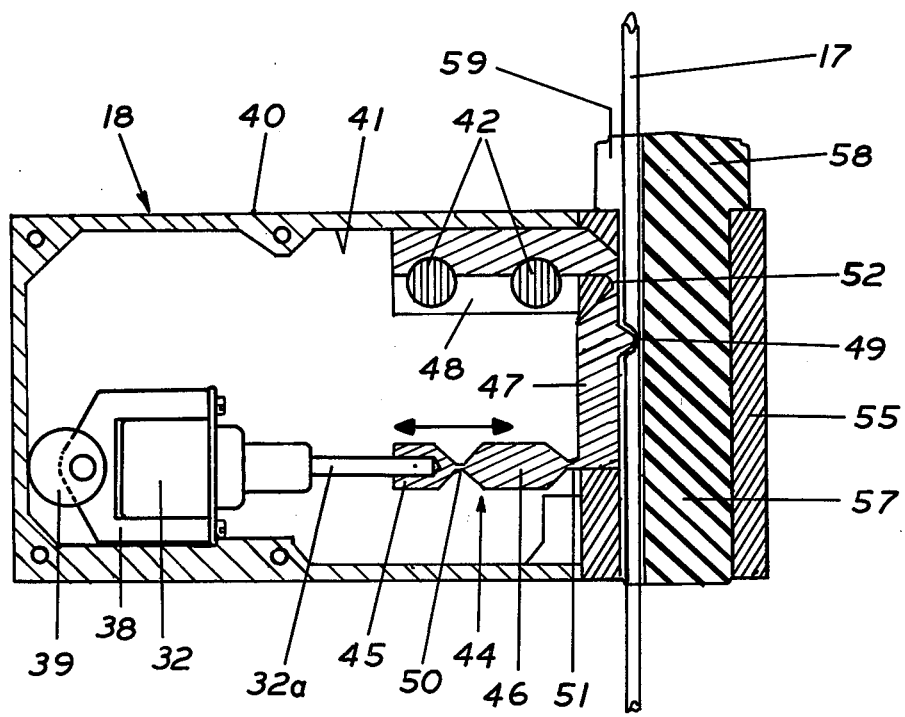
FIG. 4 is a sectional view in side elevation showing details of the constriction means.

The constriction and motor drive means are shown in greater detail in FIG. 4, and include the stepper motor 32 and shaft 32a (AIR-PAX K92121-P2) that produces a linear, incremental motion. The motor is surrounded by a yoke 38 driven from an eccentric 39, and is housed in a body 40 having an inside wall 41 and studs 42. The shaft 32a is attached to a moveable end of an elastic linkage 44 that is constructed of alternate segments of thick, rigid elements 45, 46, 47 and 48, a rigid, tapered constriction element 49, and thin flexible elements 50, 51 and 52. These segments are manufactured of a suitable extruded polymer such as polypropylene. The linkage is secured at its fixed end between the inside wall 41 and the studs 42. In thin section, the flexible elements 50, 51 and 52 will retain their flexible properties for a long time without requiring replacement.

When the motor 32 is actuated by the microprocessor, the motor shaft 32a will move the linkage 44 in the direction shown by the arrows. Since the linkage is of the motion reducing, force amplifying type, the constriction element 49 of the linkage will be urged into or away from the intravenous feed tube 17 to maintain the flow of fluid 12. Use of the eccentric 39 and yoke 38 arrangement permits withdrawal of the motor and flexible linkage from the I.V. tube and reinsertion, without changing the position of the constriction element 49 when the I.V. infusion is restarted. This enables the I.V. tube to be removed and replaced while maintaining the same constriction position.

The linkage 44 does not produce a backlash or coulomb friction, and when used in conjunction with the motor 32 which provides say, $\frac{1}{2}$ mil linear increments, the linkage enables these increments to be reduced to 1/6 mil. Typical intravenous tube sizes vary from about 130–175 mils in diameter, and a bore of about 100 mils is common.

Figure 3:
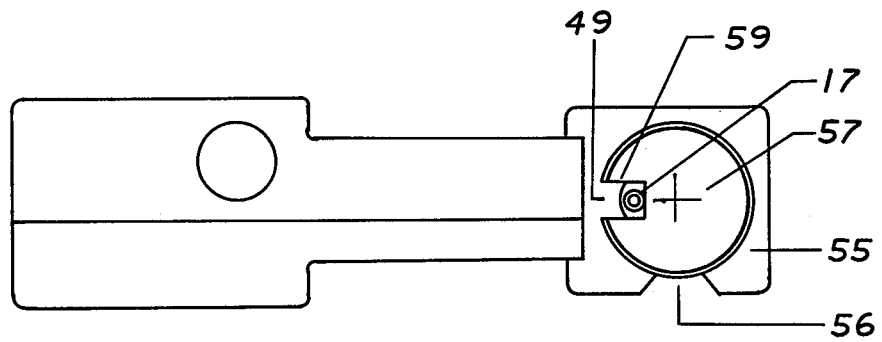
FIG. 3 is a plan view in section showing details of the constriction means.

A positively controlled tube retention means is provided for the intravenous feed tube 17, and as shown in FIGS. 3 and 4, the constriction means 18 also enables the intravenous feed tube to be aligned with the constriction element 49 of the linkage 44. The alignment system includes a hollow guide housing 55 having a vertical slot 56 and a rotatable alignment cylinder 57 is positioned within the guide housing. At its upper end, the alignment cylinder 57 provides a turning knob 58, and a vertical slot 59 is defined along the exterior of the cylinder. When the tube 17 is inserted into the vertical slot 59, and the knob is rotated to the closed position, the tube 17 will lock into the guide housing. In this position, the tube 17 will be exposed to the action of the constriction element 49 as shown in FIG. 3.

The strain gauge load cell 13 employed in the intravenous feed system of this invention is shown in FIG. 5, and includes a proving ring 60 integral with a base 61; the support hook 14 is attached to the proving ring at its upper end. A tubular member 62 is used to limit ring distortion within acceptable levels if overload occurs. Strain gauges 64, 65, 66 and 67 are used to measure the weight of the container 11, and suitable strain gauges are sold by Vishay, Micro Measurements Division as MA Series 350 OHM. The vertical center of gravity lines of the proving ring 60, hooks 14, 14a, the container 11, and the housing for the entire device are all co-axial to ensure physical stability.

The output from the intravenous control system can be maintained at about $\pm 1\%$. The graph of flow rate versus constriction opening is shown in FIG. 6, and as previously noted, the data therein, or similar non-linear data is contained in the look-up table 21.

Obviously, other equivalents of this invention may be used without departing from the spirit thereof. For example, the force of gravity feed may be supplemented by well known mechanical or pneumatic pressurizing devices for flexible I.V. containers. Also, the microprocessor may be replaced by various discrete I.C. components. Furthermore, the time intervals for the weight readings may be varied, depending on the short term perturbation times of the equipment.

I claim:

1. An intravenous feed system, comprising:
   A. a free hanging container for intravenous fluid, including a gravity feed outlet to a flexible, intravenous tube, and constriction means for the said tube;
   B. sensing means for detecting a weight change in the free hanging container to produce an analogue signal when intravenous fluid is fed therefrom;
   C. means for converting the analogue signal into digital pulses;
   D. clock means for determining $\Delta t$;
   E. a plurality of microelectronic circuit registers to receive and output digital pulses, including:
      i. an input register for receiving preset data for dw/dt flow rate and weight settings;
      ii. accumulating registers to store updated container weight and constriction settings; and,
      iii. output registers for outputting updated constriction settings, flow rate data, fluid weight data and alarm data;
   F. a ROM, including:
      i. a look-up table for determining updated constriction settings;
      ii. a sequencing memory for converting input and instruction information into address words;
      iii. a control sequence memory for generating program steps and jump pulses to control output operations; and,
   G. an arithmetic unit for:
      i. determining $\Delta w$, and dw/dt as measured;
      ii. comparing the measured dw/dt with the preset dw/dt; and,
      iii. determining the revised constriction settings based on the look-up table.

2. The intravenous system of claim 1, in which the sensing means is a strain gauge.

3. The intravenous control system of claim 1, adapted to provide an alarm signal for the following conditions: low battery, reaching the preset amount of fluid in the container, and flow rate deviation from the preset flow rate.

4. The intravenous control system of claim 1, which is battery powered.

5. The intravenous system of claim 1, in which:
   A. clock means are provided for determining $\Delta t$;
   B. the ROM memory includes:
      i. a look-up table for determining updated constriction settings;
      ii. a sequencing memory for converting input and instruction information into address words;
      iii. a control sequence memory for generating program steps and jump pulses to control output operations; and,
   C. an arithmetic unit for:
      i. determining $\Delta w$, and dw/dt as measured;
      ii. comparing the measured dw/dt with the preset dw/dt; and,
      iii. determining the revised constriction settings based on the look-up table.

6. The intravenous feed system of claim 1, including a housing for the system and a container support, the housing, support, container and sensing means being axially aligned along a common vertical center of gravity axis.

7. The intravenous feed system of claim 6, including a motor in the feedback control, the motor being adapted to apply a constrictive force against the intravenous tube.

8. The intravenous feed system of claim 7, including a motion reducing, force amplifying linkage driven by the motor, and adapted to constrict the intravenous tube.

9. The intravenous feed system of claim 8, in which the motor is a linear stepper motor.

10. The intravenous feed system of claim 9, including means to compare total fluid weight fed from the container with the preset weight of fluid to be fed.

11. The intravenous feed system of claim 10, including a motion reducing, force amplifying linkage driven by the motor, and adapted to constrict the intravenous tube, the linkage being flexible and comprising thick rigid sections and alternate sections of bendable material.

12. The intravenous feed system of claim 11, in which the linkage is extruded polypropylene.

13. An intravenous feed system, including a free hanging container for intravenous fluid, a gravity feed outlet from the container to a flexible, intravenous tube, and constriction means for the said tube to control fluid flow rate therethrough, comprising:
   A. sensing means for detecting a weight change in the free hanging container to produce an analogue signal when intravenous fluid is fed therefrom;
   B. means for converting the analogue signal into digital pulses;
   C. a plurality of microelectronic circuit registers to receive and output digital pulses, the registers being adapted to: receive preset data for flow rate settings, store updated container weight data and constriction settings, and output constriction settings; and,
   D. ROM memories adapted to: calculate revised constriction settings, and access and control constriction settings.

14. The intravenous feed system of claims 1 or 13, in which the microelectronic circuit registers and ROM memories are incorporated in a microprocessor.

15. The intravenous feed system of claim 13, including a positively controlled intravenous tube retention means associated with the constriction means.

16. The intravenous feed system of claim 15, including a guide tube and a rotatable, vertically disposed cylinder within the tube, the cylinder defining a peripheral, axial slot adapted to engage the intravenous tube and then rotate and guide the tube into contact with the constriction means.

17. The intravenous feed system of claim 16, in which the linkage is plastic and includes a tapered wedge element adapted to apply a constrictive force against the intravenous tube.

18. The intravenous feed system of claim 13, in which the total weight of fluid to be fed is compared with a preset weight of fluid fed from the container, thereby indicating when the total weight of fluid reaches the preset weight.

19. The intravenous feed system of claim 13, including a housing for the system and a container support, the housing, support, container and sensing means being axially aligned along a common vertical center of gravity axis.

20. The intravenous system of claim 13, including a motion reducing, force amplifying linkage driven by a linear stepper motor, and adapted to constrict the intravenous tube.

* * * * *